United States Patent [19]
Fischer et al.

[11] 3,962,450
[45] June 8, 1976

[54] COMPOSITION AND METHODS FOR EFFECTING SEDATION

[75] Inventors: Lawrence J. Fischer; John J. Ambre, both of Iowa City, Iowa

[73] Assignee: State of Iowa for use and benefit of the University of Iowa, Iowa City, Iowa

[22] Filed: Aug. 29, 1973

[21] Appl. No.: 392,571

[52] U.S. Cl............................ 424/267; 260/281 G
[51] Int. Cl.²........................................ A61K 31/445
[58] Field of Search ............ 260/281; 424/263, 267

[56] References Cited
UNITED STATES PATENTS 2,749,346    6/1956    Hoffmann et al................... 260/281

*Primary Examiner*—Stanley J. Friedman
*Attorney, Agent, or Firm*—Beveridge, DeGrandi, Kline & Lunsford

[57] ABSTRACT

4-Hydroxy-2-ethyl-2-phenyl glutarimide of the structure

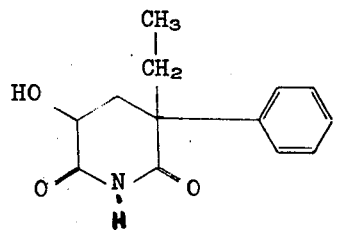

is obtained in a metabolic process and has been determined to possess biological activity similar to, but more intense than, its parent drug, glutethimide, in mammals.

3 Claims, No Drawings

COMPOSITION AND METHODS FOR EFFECTING SEDATION

The invention described herein was made in the course of work under a grant or award from the Department of Health, Education, and Welfare.

DESCRIPTION

This invention pertains to the compound 4-hydroxy-2-ethyl-2-phenyl glutarimide, its preparation and use. More particularly, the compound 4-hydroxy-2-ethyl-2-phenyl glutarimide is represented by the following structural formula:

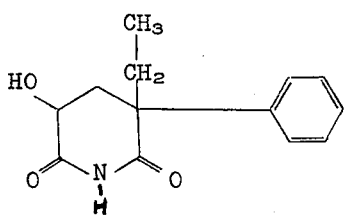

The compound, 4-hydroxy-2-ethyl-2-phenyl glutarimide is related to alpha-pheyl-alpha-ethyl-glutarimide, conventionally named glutethimide, which is a sedative-hypnotic drug. Glutethimide is similar in structure to the barbiturates. Glutethimide intoxication has become relatively common as a result of its popularity with prescribing physicians and drug-users. Although similar to the intoxicated state produced by barbiturates, glutethimide-induced coma is characterized by an unusually long duration, unexplained variations in depth and a "rebound" recurrence as the person appears to the recovering.

The pattern of metabolism of glutethimide is the same in dogs and rats, as disclosed by Keberle et al., in *Helv. Chim. Acta*, 42, pages 417 425 and in human subjects, as disclosed by Butikofer, et al., in *Arch. Exp. Path. U. Pharmak.*, 244, pages 97 to 108 (1962). In order to determine whether this similarity in metabolism among species exists after intoxicating doses, studies directed to determining the plasma levels of the drug and its metabolites in humans hospitalized on account of overdoses of glutethimide and in dogs and rats given toxic doses of glutethimide have been reported by J. J. Ambre and L. J. Fischer, in *Res. Commun. Chem. Path. Pharmacol.*, 4, pages 307 to 325 (1972), which is incorporated herein by reference. In the Ambre and Fischer paper, comparisons were made of human patients hospitalized due to glutethimide intoxication and of dogs who had been experimentally caused to ingest glutethimide. Particularly, studies of the plasma of the intoxicated patients and studies of the plasma of dogs induced to ingest glutethimide were undertaken. It was discovered by virtue of the comparison of the glutethimide metabolite components in the plasma, that dogs, rats and humans metabolize glutethimide in a different manner. Analysis of the plasma of dogs, rats and humans revealed that an hydroxy metabolite accumulated to high concentrations in humans but not in the dog and rat.

The end product metabolites of the metabolism of glutethimide was determined and reported as early as 1962 by Keberle et al., in *Experentia*, Vol. XVIII, page 105 (1962). By end-product metabolites is meant the form in which the metabolites of glutethimide are excreted. The metabolic pathway for the metabolism of glutethimide is reported in *Experentia*, Vol. XVIII, 1962, as set forth below:

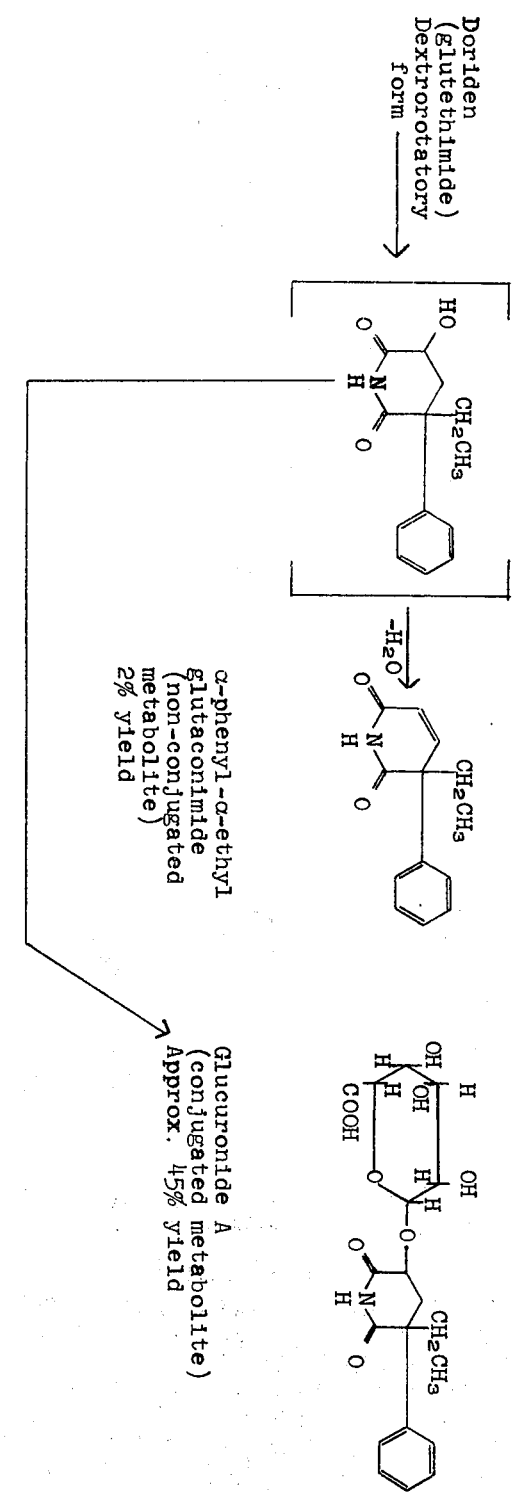

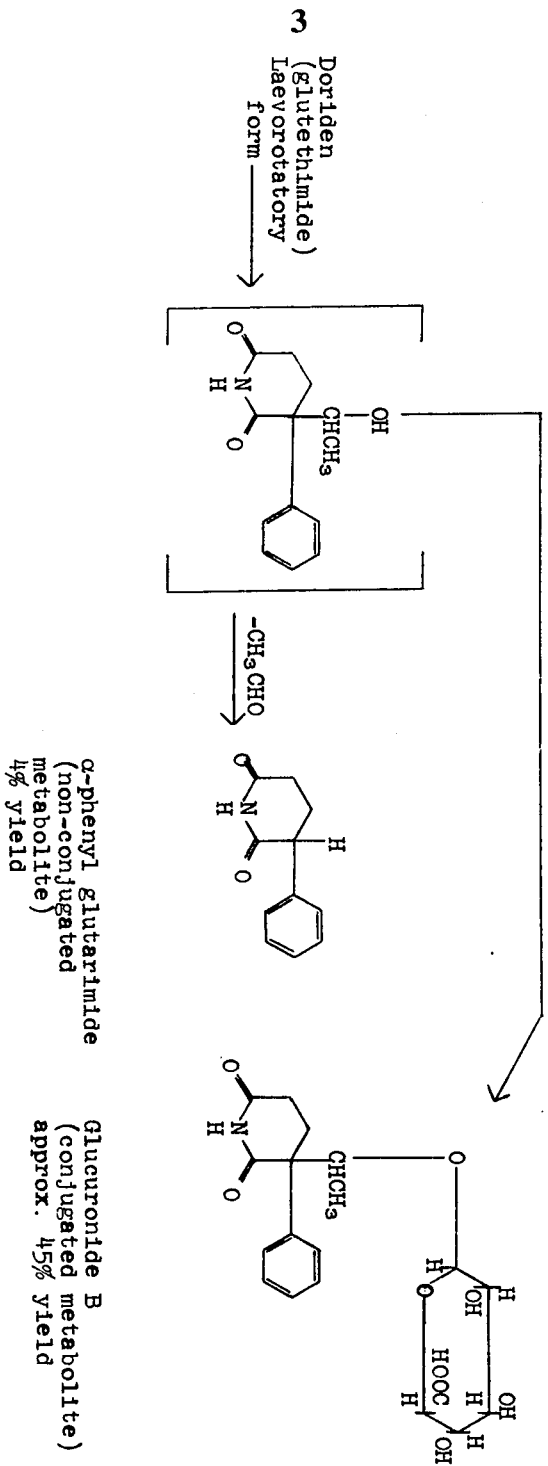

The article in *Experentia*, Vol. XVIII, pages 1 through 18 (1962) is incorporated herein by reference.

THE INVENTION

As stated above, this invention pertains to the compound 4-hydroxy-2-ethyl-2-phenyl glutarimide and the preparation thereof. This compound can also be named as 3-phenyl-3-ethyl-5-hydroxy-2,6 dioxopiperidine. The preparation of 4-hydroxy-2-ethyl-2-phenyl glutarimide is carried out in a plurality of steps. Its activity as a sedative was ascertained by testing on mammals.

The compound, 4-hydroxy-2-ethyl-2-phenyl glutarimide is prepared by a biosynthetic route by isolation from the urine of dogs given large doses of glutethimide.

Large doses of glutethimide are fed to mammals and the urine collected over a period of several days. Thereafter an acid hydrolysis reaction is carried out by contacting the collected urine with a mineral acid such as hydrochloric acid at elevated temperatures. After a period of, say, about one hour the mixture is cooled to room temperature and extracted with a suitable solvent. Two extractions with ethyl ether are satisfactory for this purpose. The solvent is evaporated and the dark brown oil obtained by this procedure is then subjected to separation as by chromatographic methods. Verification of the structure of the final product is by IR and NMR spectroscopy.

The compound was tested to verify sedative activity by procedures described hereinafter.

DETAILED DESCRIPTION

The biosynthetic preparation of 4-hydroxy-2-ethyl-2-phenyl glutarimide was undertaken as follows: mongrel dogs were caused to ingest 400 mg/kg if glutethimide conventionally sold as Doriden by Ciba. The urine of the two 20 kg mongrel dogs was collected. The urine was collected for five days in vessels chilled in ice. The animals in the experiment eventually recovered after being in a coma for approximately 24 hours after the large dose of glutethimide.

The dog urine was pooled. The urine was acidified and heated at elevated temperatures. To a 100 ml. portion of pooled dog urine containing glutethimide metabolites was added 100 mls. of 6 N HCl and the solution was heated at 100°C. for one hour. Other mineral acids which would not interfere with the isolation of the end product may be used in this acid hydrolysis step. Thereafter, the mixture was cooled to room temperature and extracted twice with a substantially water-insoluble solvent. Preferably ethyl ether is employed in this step, although other water-insoluble solvents, such as other ethers, pentane, hexane, benzene and the like may be substituted for ethyl ether. The ether extracts of the heat and acid treated urine were combined.

Isolation of the desired product may be undertaken by any of the conventional prior art techniques, such as gas liquid chromatography, crystallization and recrystallization and the like.

By way of example the desired product was isolated by silica gel column chromatography. Thus, the ether extracts of the acidified and heated glutethimide metabolites were combined and the solvent evaporated to yield a dark brown oil. Columns were prepared by making a slurry of silica gel (chromatographic grade, Type I, 60-200 mesh, Sigma Chemical Company, St. Louis, Missouri) with an eluting solvent mixture which was conveniently a 9:1 chloroform-acetone mixture. A glass column of 2 centimeters diameter was filled to a height of 45 centimeters. The residue, a residual brown oil which resulted from solvent evaporation of the acidified glutethimide metabolites, was dissolved in 1 to 2 milliliters of the eluting solvent mixture was applied to the top of the silica gel column. Eluting solvent mixture of constant composition was passed through the column at a flow rate of 3 to 4 mls. per minute. Five to 10 ml. fractions were collected and monitored by gas chromatography for the presence of the metabolite. The elutate fractions containing the metabolite (No. 20-70) were combined, and the solvent mixture, evaporated. The resulting residue, a light brown oil, was dissolved in an alcoholic solvent, preferably methanol, for application to thin-layer plates.

The methanol solution of the silica gel column eluate containing the metabolite was applied to 20 × 20 cm silica gel G plates of 250 μ thickness. Application of the material in a thin streak was facilitated by the use of the Camag chromatocharger (Camag, Inc., New Berlin, Wisconsin). The plates were then developed in a solvent system which consisted of hexane, ethyl ether and acetic acid (70:30:8). The location of the metabolite on the developed plate was determined by spraying one edge with a one percent mercurous nitrate reagent solution to yield a gray color. The band of silica containing the metabolite was scraped from the plate and the metabolite was eluted from the silica by shaking with ethyl ether. After centrifuging to remove silica gel, the ether eluates were combined.

The procedure described above was repeated on 100 ml aliquots of urine until all of the dog urine had been processed. The combined eluates from thin layer scrapings were evaporated and the residue placed in a vacuum desiccator overnight. Yellow crystals formed in the residue. The crystals and some residual oil were dissolved in a minimum amount of ethyl ether (or acetone) and a white product (approximately 100 mgs.) crystallized at −5°C. over a period of 14 days.

The chemical structure of the isolated materials was determined by IR and NMR spectroscopy. The IR spectrum shows an OH stretching band at 3530 $cm^{-1}$. The NMR shows a methine proton appearing at $\delta = 4.2$ (PPM) which because of its downfield position in the spectra, shows that the hydroxyl group is next to the carbonyl group of the imide ring. The melting point of the product is 120°–121°C.

The biological activity of the metabolite was assessed in mice using the rotating rod technique set forth in an article by Sofia, R.D., *J. Pharm. Sci.*, Vol. 58, pages 900 through 901, (1969) which is incorporated herein by reference. intraperitoneal injections were given to mice and the median effective dose ($ED_{50}$) was calculated according to the method of Litchfield and Wilcoxon, *J. Pharmacol. Exp. Ther.*, 96, pages 99 to 112 (1949) which article is incorporated herein by reference. The $ED_{50}$ for hydroxyglutethimide was 24 mg/kg with 95% confidence limits being 17 to 35 mg/kg. This compared to an $ED_{50}$ of 47 mg/kg for glutethimide using the same tests. A dose of 50 mg/kg given IP was used to anesthetize rats for a period of approximately one hour. It is possible that this material, 4-hydroxy-2-ethyl-2-phenyl glutarimide, may be used as a shorter-acting, less toxic sedative-hypnotic drug than current drugs now in use.

The description and preparation of the 4-hydroxy-2-ethyl-2-phenyl glutarimide, set forth above, is presented by way of illustration and example. It is apparent that there has been provided, in accordance with the invention, the compound 4-hydroxy-2-ethyl-2-phenyl glutarimide and a preparation thereof that fully satisfies the object, aims and advantages set forth above. While the invention has been described in conjunction with specific embodiments thereof, it is evident that many alternatives, modifications, and variations will be apparent to those skilled in the art in the light of the foregoing description. Accordingly, it is intended to embrace all such alternatives, modifications, and variations as fall within the spirit and broad scope of the appended claims.

What is claimed is:

1. A composition comprising an anesthetic dose of 4-hydroxy-2-ethyl-2-phenyl glutarimide and a pharmacologically inactive carrier therefor.

2. A method for sedation comprising treating a mammal with an effective dose of 4-hydroxy-2-ethyl-2-phenyl glutarimide.

3. A method as defined in claim 2 wherein the mammal is treated by intraperitoneal injection.

* * * * *